United States Patent [19]

Bitterli

[11] 4,316,032
[45] Feb. 16, 1982

[54] OXIMINO-IMINO-ISOINDOLINE METAL COMPLEXES USEFUL AS PIGMENTS

[75] Inventor: Peter Bitterli, Reinach, Switzerland

[73] Assignee: Sandoz Ltd., Basel, Switzerland

[21] Appl. No.: 144,382

[22] Filed: Apr. 28, 1980

[30] Foreign Application Priority Data

May 2, 1979 [CH] Switzerland .................. 4097/79

[51] Int. Cl.³ .................. C09B 57/10; C09B 57/04
[52] U.S. Cl. .................. 548/109; 260/326.1; 260/326 E; 260/326 N; 260/326 S; 260/326.22; 260/326.5 A; 260/326.47; 260/326.5 SA; 260/326.9; 548/193; 548/266; 106/288 Q
[58] Field of Search .................. 548/101, 109; 260/326.1, 326.5 A, 326.9, 326.5 E, 325 PH, 326 E, 326.22

[56] References Cited

U.S. PATENT DOCUMENTS

| 3,758,497 | 9/1973 | Pugin et al. | 260/325 PH |
| 3,897,439 | 7/1975 | Frey | 548/101 |
| 3,917,641 | 11/1975 | Bitterli et al. | 260/325 PH |
| 3,919,202 | 11/1975 | Diana | 260/326.1 |
| 3,971,805 | 7/1976 | Model | 260/325 PH |
| 4,006,162 | 1/1977 | Model et al. | 260/325 PH |
| 4,065,462 | 12/1977 | Frey et al. | 548/101 |
| 4,122,261 | 10/1978 | Crounse et al. | 544/64 |

FOREIGN PATENT DOCUMENTS

881408  11/1971  United Kingdom ............. 260/326.9

OTHER PUBLICATIONS

Sekiguchi et al., Chemical Abstracts, vol. 83, 149083a (1975).

Sekiguchi et al., Chemical Abstracts, vol. 84, 61196z (1976).

Primary Examiner—Donald G. Daus
Assistant Examiner—Diana G. Rivers
Attorney, Agent, or Firm—Gerald D. Sharkin; RIchard E. Vila; Thomas C. Doyle

[57] ABSTRACT

The present invention relates to the compounds of formula I

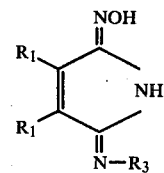

and metal complexes thereof, in which both $R_1$'s are hydrogen or halogen or form a condensed ring of the benzene series, or —S—CH$_2$CH$_2$—S—, and $R_3$ is hydrogen, a mono- or dicyclic-aromatic group or is a divalent radical of the phenylene or naphthalene series linking one further compound of formula I, wherein $R_3$ is a direct bond and the $R_1$ groups are the same as or different from the $R_1$ groups of the first compound of formula I, which metal complexes are either 1:1 metal complexes when $R_3$ is a divalent linking radical, or 1:2 metal complexes of monomeric compounds of formula I such 1:2 complexes being symmetric or asymmetric and the metal is a divalent transition metal, the complexes are useful as pigments.

9 Claims, No Drawings

OXIMINO-IMINO-ISOINDOLINE METAL COMPLEXES USEFUL AS PIGMENTS

The present invention relates to oxime compounds, their preparation and use.

More particularly, the present invention provides compounds of formula I $$\begin{array}{c} \text{NOH} \\ R_1 \diagdown \phantom{xx} \| \\ \phantom{xxxx} \diagup \phantom{xx} \diagdown \\ \phantom{xxxxxxxx} \text{NH} \\ R_1 \diagup \phantom{xxxx} \diagup \\ \phantom{xxxxx} \| \\ \phantom{xxxx} \text{N} - R_3 \end{array} \qquad \text{I}$$

and metal complexes thereof,
in which both $R_1$'s are hydrogen or halogen or form a condensed ring of the benzene series, or $-S-CH_2CH_2-S-$, and
$R_3$ is hydrogen, a mono- or dicyclicaromatic group or is a divalent radical of the phenylene or naphthalene series linking one further radical of formula I, wherein $R_3$ is a direct bond and the $R_1$ groups are the same as or different from the $R_1$ groups of the first compound of formula I,
which metal complexes are either 1:1 metal complexes when $R_3$ is a divalent linking radical, or 1:2 metal complexes of monomeric compounds of formula I such 1:2 complexes being symmetric or asymmetric and the metal is a divalent transition metal.

When the $R_1$'s form a condensed ring of the benzene series, such a ring is preferably an unsubstituted condensed benzene ring or a condensed benzene which is substituted by a total of up to 4 substituents selected from chlorine and bromine atoms or is monosubstituted by a nitro group.

When $R_3$ is a mono- or dicyclic-aromatic group it is preferably a group of the phenyl, naphtyl, triazolyl or thiazolyl series. More preferably any such aromatic group as $R_3$ is phenyl optionally substituted by up to three substituents selected from the group consisting of chlorine, bromine, methyl and methoxy or phenyl monosubstituted by benzoylamino or N-phthalimido; triazolyl; or thiazolyl. Preferably any such substituted phenyl is substituted by up to two substituents selected from chlorine and methyl or by a single substituent selected from methoxy, benzoylamino or N-phthalimido.

Preferred divalent radicals of the phenylene series are 1,3- and 1,4-phenylene optionally substituted by a total of up to two substituents selected from chlorine, bromine, methyl, methoxy and nitro, more preferably any divalent phenylene is unsubstituted 1,3- or 1,4-phenylene.

The preferred divalent radicals of the naphthalene series are unsubstituted 1,4- and 2,6-naphthalenes.

The complex forming metals may be any divalent transition metal preferably the metal is divalent nickel cobalt or copper.

Preferably both $R_1$ groups are $R_1'$, where both $R_1'$ groups are hydrogen or halogen or together they form a condensed benzene ring optionally substituted by up to 4 substituents selected from chlorine and bromine atoms or is monosubstituted by a nitro group or they form $-SCH_2CH_2S-$. More preferably both $R_1$ groups are $R_1''$, where both $R_1''$ groups together form a condensed benzene ring optionally substituted by two or four chlorine atoms.

In the compounds of formula I, when $R_3$ is a divalent linking radical preferably all the $R_1$'s are the same.

$R_3$ is preferably $R_3'$, where $R_3'$ is hydrogen; phenyl optionally substituted by up to two substituents selected from chlorine and methyl or monosubstituted by methoxy, benzoylamino or N-phthalimido; triazolyl; or triazolyl; or $R_3'$ is 1,3- or 1,4-phenylene. More preferably $R_3$ is hydrogen.

The preferred 1:2 complexes of formula I are the symmetrical complexes i.e. those where the $R_1$'s and the $R_3$'s are the same. The metal complexes of the invention may be mono or mixed metal complexes.

It is believed that the metal complexes of the compounds of formula I are of formula $$\begin{array}{c} \phantom{xxxx} H \phantom{xxxxxxxxxxx} H \\ \phantom{xxx} N-O \diagdown \phantom{xxxxx} \diagup O-N \\ R_1 \diagdown \| \phantom{xxxxx} \diagdown \diagup \phantom{xxxxx} \| \diagup R_1 \\ \phantom{xxxxxxx} N-\text{Me}-N \\ R_1 \diagup \phantom{xxxxxxxxxxxxxxx} \diagdown R_1 \\ \phantom{xxx} \| \phantom{xxxxxxxxxxxxxxxxx} \| \\ \phantom{xx} N-R_3 \phantom{xxxxxxxxxxx} R_3-N \end{array}$$

in which the $R_1$'s are the same or different and each $R_3$, independently, is hydrogen or mono- or dicyclic-aromatic group
or, one $R_3$ is a divalent radical of the phenylene or naphthalene series and the other $R_3$ is a direct bond.

Preferred compounds of formula I are those in which $R_1$ is $R_1'$ and $R_3$ is $R_3'$ and all $R_1$ groups are the same. More preferred compounds are those where $R_1$ is $R_1'$ and $R_3$ is hydrogen.

Preferred nickel, cobalt and copper complex of the compounds of formula I are those in which all $R_1$ groups are $R_1'$ and $R_3$ is $R_3''$ where each $R_3''$ is hydrogen; phenyl optionally substituted by up to two substituents selected from chlorine, methyl or monosubstituted by methoxy; benzoylamino or N-phthalimido; triazolyl; or thiazolyl; or one $R_3''$ is 1,3- or 1,4-phenylene and the other is a direct bond. More preferred complexes are those where each $R_3$ is hydrogen and all $R_1$ groups are $R_1''$.

The present invention also provides a process for the production of compounds of formula I and the metal complexes thereof which comprises (a) condensing a compound of formula III $$\begin{array}{c} \phantom{xx} R_2 \\ \phantom{xx} \| \\ R_1 \diagdown \phantom{xx} \diagup \\ \phantom{xxxx} \diagdown \phantom{xx} \text{NH} \\ R_1 \diagup \phantom{xx} \diagdown \\ \phantom{xxx} \| \\ \phantom{xx} N-R_3 \end{array} \qquad \text{III}$$

in which $R_2$ is $=NH$ or $=(OC_{1-4}alkyl)_2$ with a hydroxyl-ammonium salt, to obtain a compound of formula I, (b) metallizing a compound of formula I or a mixture thereof, with a salt of a divalent transition metal or a mixture of metal salts.

The metallization is effected in accordance with known methods. The condensation of the compound of formula III may be effected in analogy with known methods. Condensation is preferably carried out in the presence of a solvent in which the compound of formula III is at least partially soluble, for example water or preferably dimethylformamide. The condensation is generally effected at temperatures in the range of from 20° to 100° C.

The compounds of formula III are known or may be prepared by known methods from available starting materials.

The metal complexes according to the invention are useful as pigments for the mass pigmenting of synthetic plastics and resins free from or containing solvents, e.g. viscose, cellulose acetate, polyethylene, polystyrene, polyvinyl chloride, synthetic rubber and synthetic leather; of surface coatings, such as paints, whether oil or waterbased, lacquers and inks. They may also be used for pigment printing, textile coating and for pigmenting paper in the mass. Such application pigmenting is carried out in accordance with known methods. The pigmented products have good light fastness, weather fastness, resistance to chemicals, migration fastness, resistance to bleeding, fastness to overlacquering and solvents. The pigments give intense dyeing and have good application properties e.g. resistance to flocculation, crystallization and dispersion and have good covering power.

The properties of the pigments can often be improved by treating the raw pigment in organic solvents at elevated temperatures e.g. 110° to 200° C. Suitable organic solvents are those in which the pigment itself is not dissolved e.g. chlorobenzenes (mixtures), nitrobenzene, dimethylformamide, glacial acetic acid, ethylene glycol and quinoline.

The following Examples further serve to illustrate the present invention. In the Examples all parts are by weight and all temperatures are in degrees Centigrade.

EXAMPLE 1

20 Parts, 1,3-diimino-isoindoline are dissolved in 100 parts dimethylformamide and are stirred with 14 parts hydroxylammoniumchloride for 1 hour at 80°. The reaction mixture is poured onto 500 parts ice water, the precipitate is filtered off and washed salt-free with water. After drying 22 parts 1-oximino-3-imino-isoindoline pale yellow crystals (m.pt. 210°–214° with decomposition) are obtained.

For the complex formation 11.3 parts of the product are dissolved in 200 parts dimethylformamide at 80°. 7 Parts anhydrous sodium acetate and then 35 parts of a 2-N-aqueous nickel chloride solution are added. The orange complex forms immediately; after stirring for 1 hour at 80° the dyestuff is suction filtered, washed with hot water and dried. The pigment obtained gives brown-orange dyeings in plastics and lacquers which dyeings have good migration fastness and fastness to overlacquering as well as good light fastness.

EXAMPLE 2

28.3 Parts, 1,3-diimino-4,5,6,7-tetrachloro-isoindoline and 8.5 parts hydroxyl-ammonium sulphate are stirred in 150 parts dimethylformamide for 1 hour at 80°. After cooling the product can be filtered and washed with dimethylformamide and water to obtain pure 1-oximino-3-imino-4,5,6,7-tetrachloroisoindoline in the form of colourless crystals which up to 300° only darken but do not melt.

To form the metal complex the suspension (without intermediate isolation) is taken and 100 parts dimethylformamide are added thereto and subsequently reacted with 10 parts anhydrous sodium acetate as well as a solution of 13 parts nickelchloride ($NiCl_2.6H_2O$) in 30 parts water. The complex form immediately; after stirring for 1 hour at 80° the product is suction filtered and washed with dimethylformamide and water. 32 Parts of a bordeaux-red pigment is obtained which is suitable for dyeing plastics and lacquers to give dyeings having good light-, heat-and migration fastness and fastness to overlacquering.

EXAMPLE 3

44 Parts 1imino-3,3-diethoxy-isoindoline with 33 parts 2,5-dichloroaniline and 2 parts glacial acetic acid in 200 parts methanol are stirred at 65° under reflux for 5 hours. The precipitated sulphur-yellow 1-imino-3-(2',5'-dichlorophenylimino)-isoindoline is suction filtered at room temperature, washed with methanol and dried in vacuo at 60°. 29 Parts of this product are stirred with 7 parts hydroxylammoniumchloride in 150 parts dimethylformamide for 3 hours at 80°. After pouring onto 300 parts ice water the precipitated product is suction filtered, washed salt-free with cold water and dried in vacuo at 60°. The product 1-oximino-3-(2',5'-dichlorophenylimino)-isoindoline is in the form of pale yellow crystals which melt at 233°–238° with gas formation. 15.3 Parts of this product are stirred in 250 parts dimethylformamide at 80°. After the addition of 13 parts nickel acetate the red complex forms immediately. After stirring for 1 hour at 80° follpwed by cooling to room temperature, the product is filtered and washed salt-free with water. 14 Parts of pigment which gives dyeings in plastics and lacquers of red shades having good migration- and light fastness as well as fastness to overlacquering are obtained.

Further metal complex pigments which may be prepared in analogy with the procedures of the foregoing Examples are given in the following Table.

TABLE

| Ex. No. | Metal-free Compounds | metal complex | Shade on PVC |
| --- | --- | --- | --- |
| 4 | HON=⟨⟩(N-H)=N—⟨⟩ | Ni | scarlet |
| 5 | HON=⟨⟩(N-H)=N—⟨⟩(CH₃)(CH₃) | Ni | red |

TABLE-continued

| Ex. No. | Metal-free Compounds | metal complex | Shade on PVC |
|---|---|---|---|
| 6 | [structure: isoquinoline with HON= and =N—C₆H₄—OCH₃] | Ni | red |
| 7 | [structure: isoquinoline with HON= and =N—C₆H₄—NH—CO—C₆H₅] | Ni | scarlet |
| 8 | [structure: isoquinoline with HON= and =N—C₆H₄—N(phthalimide)] | Ni | red |
| 9 | [structure: bis-isoquinoline linked via phenylene, with NOH groups] | Ni | brown-violet |
| 10 | [structure: isoquinoline with HON= and =NH] | Cu | yellow-brown |
| 11 | " | Co | " |
| 12 | [structure: tetrachloro isoquinoline with HON= and =NH] | Co | " |
| 13 | " | Cu | yellow |
| 14 | " | Ni/Cu 1:1 | brown |
| 15 | [structure: dichloro isoquinoline with HON= and =NH] | Ni | orange |
| 16 | [structure: dichloro isoquinoline with HON= and =N—C₆H₅] | Ni | red |
| 17 | [structure: dithio-fused ring with NOH, N—H, NH] | Ni | bluish-red |
| 18 | [structure: O₂N-substituted with NOH, N—H, NH] | Ni | " |
| 19 | [structure: dichloro with NOH, N—H, NH] | Ni | red |

TABLE-continued

| Ex. No. | Metal-free Compounds | metal complex | Shade on PVC |
|---|---|---|---|
| 20 | (Cl, Cl substituted, NOH, N—H, NH) | Ni | violet |
| 21 | (Br, Br, Br, NOH, N—H, NH) | Ni | bluish-red |
| 22 | (Cl, Cl, Cl, Cl, NOH, N—H, N-triazolyl) | Ni | yellow |
| 23 | (Cl, Cl, Cl, Cl, NOH, N—H, N-thiazolyl) | Ni | orange |

APPLICATION EXAMPLE

05. Parts pigment of Example 2 and 5 parts titanium dioxide are added to a basic mixture containing:
63 parts polyvinylchloride-emulsion
32 parts dioctylphthalate
3 parts conventional epoxy softener
1.5 parts stabiliser (conventional barium-cadmium-stearate mixture) and
0.5 parts conventional chelator
and the whole is mixed to homogenety. The mixture is rolled on a mixing roller apparatus heated to 160° having friction roller (one roller with 20 rotations and the other with 25 rotations per minute) for 8 minutes, the foils of 0.3 mm which have a bluish-red shade are taken-off the rollers.

What is claimed is:

1. A metal complex of a compound of formula I

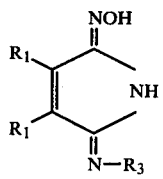

in which
both $R_1$'s are hydrogen or halogen or together form $-S-CH_2-CH_2-S-$ or a condensed benzene ring which is unsubstituted or substituted by a total of up to four substituents selected from chlorine and bromine or by one nitro group, and
$R_3$ is hydrogen; phenyl; phenyl sustituted by up to three substituents selected from chlorine, bromine, methyl and methoxy or by one benzoylamino or N-phthalimido group; triazolyl; or thiazolyl; or a divalent 1,3- or 1,4-phenylene radical which is unsubstituted or substituted by a total of up to two substituents selected from chlorine, bromine, methyl, methoxy and nitro; or a divalent unsubstituted 1,4- or 2,6-naphthalene radical; which divalent radical links one further radical of formula I, wherein $R_3$ is a direct bond and the $R_1$ groups are the same as or different from the $R_1$ groups of the first compound of formula I,
which metal complex is either a 1:1 metal complex when $R_3$ is a divalent linking radical, or a symmetric or asymmetric 1:2 metal complex of monomeric compounds of formula I, and the metal is a divalent transition metal.

2. A complex according to claim 1, in which $R_3$ is $R_3'$, where $R_3'$ is hydrogen; phenyl optionally substituted by up to two substituents selected from chlorine and methyl or monosubstituted by methoxy, benzoylamino or N-phthalimido; triazolyl; or thiazolyl; or $R_3'$ is 1,3- or 1,4-phenylene.

3. A complex according to claim 2, in which when $R_3$ is a divalent radical all the $R_1$ groups are identical.

4. A complex according to claim 3, in which both $R_1$ groups form a condensed benzene ring optionally substituted by two or four chlorine atoms.

5. A complex according to claim 2, in which $R_3$ is other than triazolyl or thiazolyl.

6. A complex according to claim 4, in which $R_3$ is hydrogen.

7. A complex according to claim 1, in which the metal is divalent nickel, cobalt or copper.

8. A complex according to claim 5, in which the metal is divalent nickel, cobalt or copper.

9. A complex according to claim 6 wherein the $R_1$'s together form a condensed benzene ring substituted by four chlorine atoms and the metal is nickel.

* * * * *